United States Patent
O'Rear et al.

(10) Patent No.: US 6,667,347 B2
(45) Date of Patent: *Dec. 23, 2003

(54) SCRUBBING $CO_2$ FROM METHANE-CONTAINING GASES USING AN AQUEOUS STREAM

(75) Inventors: Dennis J. O'Rear, Petaluma, CA (US); Curtis Munson, Oakland, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/951,551

(22) Filed: Sep. 14, 2001

(65) Prior Publication Data

US 2003/0055116 A1 Mar. 20, 2003

(51) Int. Cl.$^7$ .................. C07C 27/00; E21B 43/00; B01D 47/04
(52) U.S. Cl. ................. 518/700; 518/702; 166/267; 95/150
(58) Field of Search ................. 518/700, 702; 95/150; 166/267

(56) References Cited

U.S. PATENT DOCUMENTS

| | | | |
|---|---|---|---|
| 4,093,029 A | | 6/1978 | Weisz et al. |
| 4,322,227 A | * | 3/1982 | Cook et al. .................. 95/150 |
| 5,364,611 A | | 11/1994 | Iijima et al. |
| 5,660,603 A | | 8/1997 | Elliot et al. |
| 6,170,264 B1 | | 1/2001 | Viteri |
| 6,190,301 B1 | | 2/2001 | Murray |
| 6,248,794 B1 | * | 6/2001 | Gieskes ....................... 518/700 |

FOREIGN PATENT DOCUMENTS

| | | |
|---|---|---|
| EP | 0 921 184 | 6/1999 |
| GB | 314842 | 7/1929 |
| GB | 2123027 | 1/1984 |
| WO | 95/20558 | 8/1995 |
| WO | 01/74472 A1 | 10/2001 |

OTHER PUBLICATIONS

John H. Perry, Chemical Engineering Handbook, 4th Edition, pp. 9–51, McGraw Hill Book Company, 1963.
E. Dendy Sloan, Jr., "Clathrate Hydrates of Natural Gases," Marcel Dekker, Inc., 1990.
John Nighswander et al., "Solubilities of Carbon Dioxide in Water and 1 wt% NaCl Solution at Pressures upto 10 Mpa and Temperatures from 80 to 200 Degrees C," J. Chem. Eng. Data, 1989, 34, 355–360.
United Kingdom Search Report dated Mar. 11, 2003.

* cited by examiner

*Primary Examiner*—J. Parsa
(74) *Attorney, Agent, or Firm*—Burns, Doane, Swecker & Mathis, L.L.P.

(57) ABSTRACT

A method for removing $CO_2$ from a gas stream, including methane and $CO_2$. The method includes contacting a gas stream with an aqueous stream, so that at least a portion of the $CO_2$ in the gas stream is dissolved into the aqueous stream, thereby creating a $CO_2$-depleted gas stream, having an enriched methane concentration, and a $CO_2$-enriched aqueous stream. The $CO_2$-enriched aqueous stream is separated from the gas stream. Finally, the $CO_2$-enriched aqueous stream is disposed of in at least one of a marine environment, a terrestrial formation or combination thereof.

18 Claims, 2 Drawing Sheets

Conventional Fischer Tropsch Synthesis

Improved Fischer Tropsch Synthesis

SCRUBBING CO₂ FROM METHANE-CONTAINING GASES USING AN AQUEOUS STREAM

BACKGROUND OF THE INVENTION

1. Field of the Invention

The present invention is directed to removing $CO_2$ from $CH_4$-containing gases. In particular, the present invention is directed to scrubbing $CO_2$ from a $CH_4$-containing gas using an aqueous stream, forming a $CO_2$-reduced $CH_4$-containing gas and a $CO_2$-enriched aqueous stream, processing the $CO_2$-reduced $CH_4$-containing gas to form salable liquid products, and disposing of the $CO_2$-enriched aqueous stream.

2. Description of the Related Art

The conversion of remote natural gas assets into transportation fuels has become more desirable because of the need to exploit existing natural gas assets as a way to satisfy the increasing need for transportation fuels. Generally, the term "remote natural gas" refers to a natural gas asset that cannot be economically shipped to a commercial market by pipeline.

Conventionally, two approaches exist for converting remote natural gases into conventional transportation fuels and lubricants including, but not limited to, gasoline, diesel fuel, jet fuel, lube base stocks, and the like. The first approach comprises converting natural gas into synthesis gas by partial oxidation, followed by a Fischer-Tropsch process, and further refining of resulting Fischer-Tropsch products. The second approach comprises converting natural gas into synthesis gas by partial oxidation, followed by methanol synthesis wherein the synthesized methanol is subsequently converted into highly aromatic gasoline by a Methanol-To-Gasoline (MTG) process. Both of these approaches use synthesis gas as an intermediate. Also, while other approaches exist for using natural gas in remote locations, such approaches do not produce conventional transportation fuels and lubricants, but instead produce other petroleum products including, but not limited to, liquified natural gas (LNG) and converted methanol. The Fischer-Tropsch and MTG processes both have advantages and disadvantages. For instance, the Fischer-Tropsch process has the advantage of forming products that are highly paraffinic. Highly paraffinic products are desirable because they exhibit excellent combustion and lubricating properties. Unfortunately, a disadvantage of the Fischer-Tropsch process is that the Fischer-Tropsch process emits relatively large amounts of $CO_2$ during the conversion of natural gas assets into salable products. An advantage of the MTG process is that the MTG process produces highly aromatic gasoline and LPG fractions (e.g., propane and butane). However, while highly aromatic gasoline produced by the MTG process is generally suitable for use in conventional gasoline engines, highly aromatic MTG gasoline may be prone to form durene and other polymethyl aromatics having low crystallization temperatures that form solids upon standing. In addition, the MTG process is more expensive than the Fischer-Tropsch process and the products produced by the MTG process cannot be used for lubricants, diesel engine fuels or jet turbine fuels.

Catalysts and conditions for performing Fischer-Tropsch reactions are well known to those of skill in the art, and are described, for example, in EP 0 921 184A1, the contents of which are hereby incorporated by reference in their entirety. A schematic of a conventional Fischer-Tropsch process is shown in FIG. 1.

The Fischer-Tropsch process can be understood by examining the stoichometry of the reaction that occurs during a Fischer-Tropsch process. For example, during Fischer-Tropsch processing, synthesis gas (i.e., a mixture including $CO_2$ and hydrogen), is generated, typically from at least one of three basic reactions. Typical Fischer-Tropsch reaction products include paraffins and olefins, generally represented by the formula $nCH_2$. While this formula accurately defines mono-olefin products, it only approximately defines $C_5^+$ paraffin products. The value of n (i.e., the average carbon number of the product) is determined by reaction conditions including, but not limited to, temperature, pressure, space rate, catalyst type and synthesis gas composition. The desired net synthesis gas stoichiometry for a Fischer-Tropsch reaction is independent of the average carbon number (n) of the product and is about 2.0, as determined by the following reaction equation:

$$nCO+2nH_2 \rightarrow nH_2O+nCH_2$$

where $nCH_2$ represents typical Fischer-Tropsch reaction products such as, for example, olefins and paraffins.

The three general reactions that produce synthesis gas from methane are as follows:

1. steam reforming of methane: $CH_4+H_2O \rightarrow CO+3H_2$;
2. dry reforming, or reaction between $CO_2$ and methane: $CH_4+CO_2 \rightarrow 2CO+2H_2$; and
3. partial oxidation using oxygen: $CH_4+1/2O_2 \rightarrow CO+2H_2$.

Although the above general reactions are the basic reactions used to produce synthesis gas, the ratio of hydrogen to carbon monoxide produced by the above reactions is not always adequate for the desired Fischer-Tropsch conversion ratio of 2.0. For example, in the steam reforming reaction, the resulting ratio of hydrogen to carbon monoxide is 3.0, which is higher than the desired hydrogen to carbon ratio of 2.0 for a Fischer-Tropsch conversion. Similarly, in the dry reforming reaction, the resulting hydrogen to carbon monoxide ratio is 1.0, which is lower than the desired hydrogen to carbon monoxide ratio of 2.0 for a Fischer-Tropsch conversion. In addition to exhibiting a hydrogen to carbon monoxide ratio that is lower than the desired ratio for a Fischer-Tropsch conversion, the above dry reforming reaction also suffers from problems associated with rapid carbon deposition. Finally, because the above partial oxidation reaction provides a hydrogen to carbon monoxide ratio of 2.0, the partial oxidation reaction is the preferred reaction for Fischer-Tropsch conversions.

In commercial practice, an amount of steam added to a partial oxidation reformer can control carbon formation. Likewise, certain amounts of $CO_2$ can be tolerated in the feed. Thus, even though partial oxidation is the preferred reaction for Fischer-Tropsch conversions, all of the above reactions can occur, to some extent, in an oxidation reformer.

During partial oxidation, $CO_2$ forms because the reaction is not perfectly selective. That is, some amount of methane in the reaction will react with oxygen to form $CO_2$ by complete combustion. The reaction of methane with oxygen to form $CO_2$ is generally represented by the following reactions:

$$CH_4+O_2 \rightarrow CO_2+2H_2$$

and $$CH_4+2O_2 \rightarrow CO_2+2H_2O.$$

Furthermore, steam added to the reformer to control coking, or steam produced during the Fischer-Tropsch reaction can react with CO to form $CO_2$ in a water gas shift reaction represented by the following general reaction:

$$CO+H_2O \rightarrow CO_2+H_2.$$

Thus, invariably a significant amount of $CO_2$ is formed during the conversion of methane into transportation fuels and lubricants by the Fischer-Tropsch process. The $CO_2$ produced during the Fischer-Tropsch process exits the Fischer-Tropsch/Gas-To-Liquid (GTL) process in a tail gas exiting a Fischer-Tropsch facility. Tail gases exiting a Fischer-Tropsch/GTL process comprise any gases that remain unconsumed by the Fischer-Tropsch process.

The above equations represent general stoichiometric equations, they do not reflect an optimum synthesis gas composition for the kinetics or selectivity of a Fischer-Tropsch reaction. Moreover, depending on the nature of the Fischer-Tropsch catalyst, synthesis gas ratios other than about 2.0, typically less than about 2.0, are used to prepare the feed to a Fischer-Tropsch facility. However, because Fischer-Tropsch facilities typically produce products exhibiting a hydrogen to carbon ratio of about 2.0, the limiting reagent, typically $H_2$, is consumed first. The extra reagent, typically CO, is then recycled back to the Fischer-Tropsch facility for further conversion. Synthesis gas compositions having hydrogen to carbon ratios other than about 2.0 are typically generated by recycling unused reagents.

As a result, there is an urgent need for a process that can reduce $CO_2$ emissions from Fischer-Tropsch GTL processes, thereby minimizing adverse environmental effects that may be caused by such emissions. Furthermore, technology is needed to enable the processing of $CO_2$-rich natural gas without the emission of the $CO_2$ associated with the gas into the environment.

SUMMARY OF THE INVENTION

The present invention satisfies the above objectives by providing a process that removes $CO_2$ from $CH_4$-containing gases and isolates the removed $CO_2$ from the environment by scrubbing with an aqueous stream. By scrubbing with an aqueous stream, the present invention avoids the need for costly $CO_2$ isolation processes.

A method, according to the present invention, for removing $CO_2$ from a gas stream can include contacting a gas stream, including methane and $CO_2$, with an aqueous stream so that at least a portion of the $CO_2$ in the gas stream is dissolved into the aqueous stream, creating a $CO_2$-depleted gas stream having an enriched methane concentration, and a $CO_2$-enriched aqueous stream. The $CO_2$-enriched aqueous stream is then separated from the gas stream. Finally, the $CO_2$-enriched aqueous stream is disposed of in, for example, at least one of a marine environment, a terrestrial formation or combination thereof.

A process of the present invention, for converting methane-containing gas in a Fischer-Tropsch GTL facility into liquid hydrocarbons can include contacting a methane-containing gas, being supplied to a Fischer-Tropsch GTL facility, with an aqueous stream so that at least a portion of $CO_2$ in the methane-containing gas is dissolved into the aqueous stream creating a $CO_2$-depleted methane-containing gas and a $CO_2$-enriched aqueous stream. The $CO_2$-enriched aqueous stream is then separated from the gas stream. Next, the $CO_2$-enriched aqueous stream is disposed of in at least one of a marine environment, a terrestrial formation or combination thereof. Finally, the $CO_2$-depleted methane-containing gas is processed in the Fischer-Tropsch GTL facility to obtain liquid hydrocarbons.

A method of the present invention for removing $CO_2$ from a gas can include contacting a gas, including methane and $CO_2$, at a pressure greater than about atmospheric pressure and less than a pressure of a source supplying the gas stream, with a $CO_2$-selective adsorbent, creating a $CO_2$-enriched adsorbent and a $CO_2$-depleted gas having an enriched methane concentration. Next, the $CO_2$-enriched adsorbent is treated to regenerate the adsorbent to be reused to contact the gas and to form a $CO_2$ stream. The $CO_2$ stream is then contacted with an aqueous stream so that at least a portion of the $CO_2$ is dissolved into the aqueous stream, producing a $CO_2$-enriched aqueous stream. Finally, the $CO_2$-enriched aqueous stream is disposed of in at least one of a marine environment, a terrestrial formation or combination thereof.

In general, the present invention removes $CO_2$ from $CH_4$-containing gases, including gases being fed to Fischer-Tropsch GTL facilities by scrubbing $CO_2$ from the gas using an aqueous stream, preferably at a pressure greater than about atmospheric pressure. Thus, one important advantage of the present invention is that it avoids having to use costly $CO_2$ isolation processes including, but not limited to, $CO_2$ compression, liquefaction or solidification to isolate $CO_2$ from $CH_4$-containing gases.

DETAILED DESCRIPTION OF THE PREFERRED EMBODIMENTS

Figure 1:
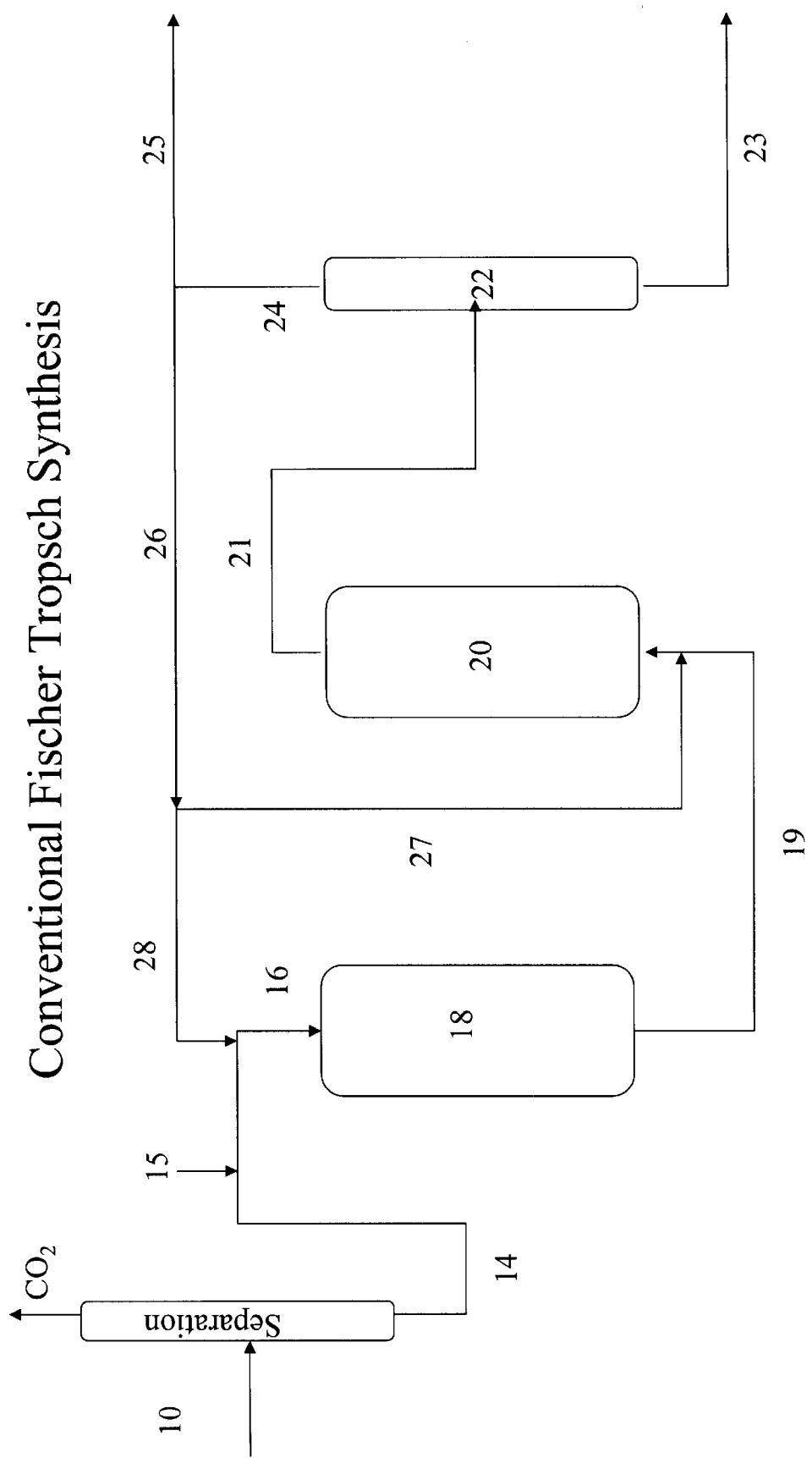
FIG. 1 is a schematic view of a conventional Fischer-Tropsch process.

In the present invention, at least a portion of $CO_2$ present in a $CO_2$-containing gas is removed and disposed of in an aqueous phase. In processes of the present invention, $CO_2$ is removed from a gas and isolated from the environment by scrubbing with an aqueous stream, preferably at a pressure greater than about atmospheric pressure in order to assist in the removal of $CO_2$.

In preferred embodiments, scrubbing is not conducted upon streams containing significant amounts of liquid hydrocarbons. In particular, scrubbing to remove $CO_2$ from streams that also contain significant amounts of liquid hydrocarbons is avoided because the presence of significant amounts of liquid hydrocarbons can make separation more difficult.

Scrubbing in preferred embodiments can be conducted using various suitable processes. In a preferred embodiment of the present invention, scrubbing is conducted by contacting a $CO_2$-containing gas stream with a $CO_2$-selective adsorbent, creating a $CO_2$-enriched adsorbent and a $CO_2$-depleted gas stream having an enriched methane concentration. The $CO_2$-enriched adsorbent is then treated so that the adsorbent is regenerated to be recycled for reuse in contacting the $CO_2$-containing gas. In addition to regenerating the adsorbent, treatment of the $CO_2$-enriched adsorbent generates a $CO_2$ stream. Treatment of the $CO_2$-selective adsorbent can be achieved using numerous suitable techniques including, but not limited to, heating or reducing the pressure of the $CO_2$-selective adsorbent. Also, while various suitable $CO_2$-selective adsorbents can be used in processes of the present invention, especially suitable $CO_2$-selective adsorbents include, but are not limited to, materials having a greater selectivity for adsorption of $CO_2$ relative to methane than water such as, for example, amines such as monoethanol amine. Following treatment of the $CO_2$-enriched adsorbent, the $CO_2$ stream is contacted with an aqueous stream so that at least a portion of the $CO_2$ is dissolved into the aqueous stream.

Because the amount of $CO_2$ that can be dissolved in an aqueous stream can be dependent on pressure, it is preferable to conduct scrubbing at elevated pressures such as, for example, pressures greater than about atmospheric pressure. It is also preferable that the pressure of the aqueous stream be less than a pressure of a source of the gas being scrubbed. For instance, in a preferred embodiment, a pressure difference between pressures of a source of the gas and an aqueous phase is at least about 10 psi.

The $CO_2$-depleted methane-containing gas produced by processes of the present invention can be used in various applications. Suitable applications include, but are not limited to, electric power generation, furnace fuel, Fischer-Tropsch GTL feedstock, combinations thereof and the like.

Once scrubbing has been conducted, the $CO_2$-enriched aqueous stream, still at an elevated pressure, can be disposed of using a suitable environmentally-friendly disposal method. Methods for the disposal of $CO_2$-enriched aqueous streams, in accordance with the present invention, include, but are not limited to, injection into a marine environment or body of water, injection into a terrestrial formation, combinations thereof and the like.

Suitable marine environments in the present application include, but are not limited to, lakes, ponds, oceans, seas, reservoirs, pools, rivers, streams, springs, combinations thereof and the like. There are also numerous terrestrial formations suitable for the disposal of $CO_2$-enriched aqueous streams in the present invention. Suitable terrestrial formations include, but are not limited to, hydrocarbonaceous formations, non-hydrocarbonaceous formations, combinations thereof and the like. Especially suitable formations include, but are not limited to, underground natural liquid and gaseous formations, coal beds, methane hydrates, combinations thereof and the like.

If the pressure required for injection in such disposal processes is greater than a pressure of the $CO_2$-enriched stream, pressure can be easily and inexpensively increased using liquid phase pumps. Ideally, the $CO_2$-enriched stream is injected at a pressure, temperature, amount of $H_2O/CH_4$ $CO_2$ and pH sufficient to ensure that the $CO_2$ does not vaporize, but remains dissolved in the liquid. For instance, temperature, pressure, amount of $H_2O/CH_4$—$CO_2$ and pH during disposal of a $CO_2$-enriched aqueous stream, are preferably sufficient to ensure that at least about 75%, more preferably at least about 85%, and most preferably at least about 90% of the $CO_2$ removed from a $CO_2$-containing gas stream remains dissolved in the aqueous phase. Generally, pressure is adjusted according to temperature and pH during disposal.

There are several sources of aqueous streams for scrubbing that are suitable for processes of the present invention. Suitable sources of aqueous streams include, but are not limited to, sea water, reaction water formed in a Fischer-Tropsch GTL process, spent cooling water from a Fischer-Tropsch GTL facility, river water or other non-potable water sources, water recovered from crude or gas production, combinations thereof and the like.

The pH of an aqueous stream used in scrubbing can also be important. Preferably, the aqueous stream, exhibits a pH that is as high as possible, preferably at least about 7.0. A high pH aqueous stream is beneficial because a high pH facilitates scrubbing of $CO_2$. The pH of the aqueous stream used for scrubbing $CO_2$ can be increased using any number of suitable techniques. Suitable techniques for increasing the pH of an aqueous stream include, but are not limited to, adding an alkali and/or other basic materials, such as ammonia. However, because these materials must be disposed of, these materials should preferably be both inexpensive and benign to the environment in which they will be disposed. Accordingly, in view of the need to minimize cost and environmental impact, preferred aqueous sources include, but are not limited to, sea water, river water, or other non-potable water sources from the environment.

Fischer-Tropsch GTL process water may be an especially suitable aqueous stream source because GTL process water is abundantly produced during Fischer-Tropsch GTL processing. For instance, when referring to the stoichiometric equation governing the conversion of synthesis gas to Fischer-Tropsch products:

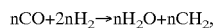
$$nCO + 2nH_2 \rightarrow nH_2O + nCH_2,$$

it can be seen that the weight ratio of water to hydrocarbon produced by the reaction is about 1.25. Thus, a typical Fischer-Tropsch GTL process produces about 25% more water than hydrocarbon, on a weight basis. Although Fischer-Tropsch GTL process water is abundantly produced, a disadvantage of using GTL process water as an aqueous stream, is that GTL process water may contain acidic contaminants, such as, for example, acetic acid and/or other organic acids. Acidic contaminants present in GTL process water can lower the pH of the water and can reduce the solubility of $CO_2$ therein. As a result, if GTL process water is used for scrubbing $CO_2$, it is preferable to remove acidic contaminants from the GTL process water before using it as a scrubbing stream. Acidic contaminants in GTL process water can be removed using various known methods. Suitable methods for removing acidic contaminants from GTL process water include, but are not limited to, distillation, adsorption onto alumina, or a basic material, and oxidation.

In addition to pH and acidic contaminant composition, it may also be important to limit the oxygen content of an aqueous stream. Preferably, an aqueous stream is de-aerated before being used, to increase the aqueous stream's capacity to adsorb $CO_2$ and to minimize air introduced into the gas stream. Suitable processes for de-aeration of aqueous streams are well known in the art and are used, for example, in desalination plants and for preparation of boiler feed water. Such processes are described in detail, for example, in John H. Perry's Chemical Engineering Handbook, 4th Edition, pages 9–51, McGraw Hill Book Company, 1963.

Since the purpose of the invention is to produce a gas stream enriched in carbon dioxide for disposal, and to produce this gas at pressures greater than atmospheric, is should be recognized that conventional amine scrubbing is not the preferred method as the amine will degrade when the temperatures of the desorber are sufficient to free the absorbed carbon dioxide from the solution. But the adsorbent does not need to be pure water. The absorbent used to remove carbon dioxide from the synthesis gas streams should not contain a significant amount of an amine (less than 1 wt %) as the amines can degrade. It is well know than various inorganic basic compounds (sodium hydroxide, potassium hydroxide, and the like) can adsorb carbon dioxide at low temperatures and desorb it as a pressurized and purified gas stream at elevated pressures and temperatures and without decomposition. Commercial processes which use these inorganic basic compounds are known as the Benfield process, the Catacarb process, the Giammarco- Vetrocoke process. These process are described in Kirk-Othmer Encyclopedia of Chemical Technology, 4th Edition, Volume 5, pages 42–46 and references contained therein.

If a $CO_2$-enriched aqueous stream, generated in the present invention, is disposed of in a terrestrial formation, disposal of the aqueous stream can be conducted in the same formation used to supply methane. In preferred embodiments, for instance, a $CO_2$-enriched aqueous stream can be disposed of in a hydrocarbonaceous formation that supplies a methane-containing gas, that may also comprise $C_2^+$ hydrocarbons. In addition, it is equally suitable to dispose of $CO_2$-enriched aqueous streams, generated by the present invention, in a terrestrial formation that differs from the formation used to supply methane. In instances where disposal is conducted in the same formation used to supply methane to the process, disposal can be conducted either at the same location where methane production is conducted or at a different location. Preferably, if disposal is conducted in the same formation as the formation used to supply methane, disposal is conducted at a location different from the location where methane is supplied in order to minimize the amount of $CO_2$ that may be returned with methane produced and supplied to the process.

Under certain conditions, it may be preferable to dispose of a $CO_2$-enriched aqueous stream in the same formation used to supply methane. For example, if the pressure of a formation needs to be maintained, it may be desirable to dispose of a $CO_2$-enriched aqueous stream in the same formation used to supply methane. Furthermore, when pressure maintenance and/or augmentation is desired, it may be beneficial for the $CO_2$ to at least partially vaporize. Preferably, $CO_2$ vaporization occurs during injection rather than before or during pumping. $CO_2$ vaporization can be achieved using various suitable processes.

One suitable way to vaporize $CO_2$ is to reduce the pH of the aqueous stream. Among the numerous possible ways to reduce the pH of an aqueous stream, suitable methods include, but are not limited to, injecting an acid into the aqueous stream. A convenient source of acid for injection into the aqueous stream is, for example, acid present in waste water produced by Fischer-Tropsch GTL processes. Accordingly, in a preferred embodiment, a $CO_2$-enriched aqueous stream is injected into a formation to both dispose of the $CO_2$ and to maintain pressure in the formation. Furthermore, an acidic stream may be injected into the formation to reduce the pH of the aqueous stream to facilitate $CO_2$ vaporization. Mixing of the acidic stream and the $CO_2$-containing aqueous stream can be conducted at various locations in the process. However, in order to minimize problems associated with compression, it is preferable to mix the acidic stream and the aqueous stream after they have been separately compressed. Mixing can take place in the formation, either using separate wells or by alternating injection of the streams, or mixing can take place above ground after the liquids have been pressurized.

In addition to reducing pH of the aqueous stream by injecting an acidic stream, one can also reduce the pH of the aqueous stream by mixing the aqueous stream with a low pH stream. For instance, the pH of an aqueous stream can be reduced by adding at least one low pH aqueous stream from a Fischer-Tropsch GTL facility.

The injection of a $CO_2$-enriched aqueous stream into a hydrocarbonaceous formation supplying methane gas may provide benefits other than formation pressure maintenance and/or augmentation. For instance, the aqueous stream may be injected, possibly with an added surfactant, into a hydrocarbonaceous formation to assist in hydrocarbon recovery and/or to displace hydrocarbons to facilitate hydrocarbon production.

If the $CO_2$-containing gas stream contains relatively low amounts of $CO_2$ in comparison with other gases, the aqueous stream may not be highly selective to scrubbing $CO_2$. In this case, it may be preferable to conduct scrubbing in stages. For instance, a first selective $CO_2$ scrubbing operation may be conducted, followed by desorption to generate a concentrated $CO_2$ gas stream. Finally, scrubbing can be conducted with an aqueous stream. Technology suitable for selective scrubbing of $CO_2$ is well known in the art and typically uses amines.

Scrubbing of $CO_2$ from methane-containing gases using aqueous liquids should be performed at non-extreme pressures to avoid formation of methane, $CO_2$ and other hydrates. The dissolution of $CO_2$ in water is favored at high pressures. Thus, it is preferable to operate at as high a pressure as possible while remaining within economic limits. Accordingly, gas compression is undesirable.

In addition to the importance of monitoring pressure during scrubbing, it may also be important to monitor temperature. For instance, at higher temperatures, hydrate formation can occur at elevated pressures. Also, at lower temperatures, gases may become more soluble in water, resulting in higher selectivity for the removal of $CO_2$ over methane and other valuable hydrocarbons.

In addition to pressure and temperature, salinity can also affect the solubility of hydrocarbons in water. For example, a larger "salting-out" effect can occur when using non-ionic hydrocarbons such as, for example, methane. Accordingly, variations in temperature and salinity of an aqueous solution can be used to maximize selectivity for $CO_2$ removal. Additionally, the presence of salt in sea water can create a slight tendency to reduce the temperature at which hydrates will form.

It is well known to those of ordinary skill in the art as disclosed, for example, in E. Dendy Sloan, Jr., "Clathrate Hydrates of Natural Gases," Marcel Dekker, Inc., 1990, that the maximum pressure that can be tolerated to avoid hydrate formation at various temperatures for methane and $CO_2$ are:

|  | Pure Methane | | Pure Carbon Dioxide | |
| --- | --- | --- | --- | --- |
| Temperature | 2° C. | 8° C. | 0° C. | 10° C. |
| Maximum Pressure, Psia | 2.9 MPa (430 psi) | 6.1 MPa (900 psi) | 1.3 Mpa (192 psi) | 14 Mpa (2000 psi) |
| Equivalent Hydrostatic Water Depth, Feed (62.4 lb/ft$_3$ water density) | 1,000 ft | 2,100 ft | 450 ft | 4,800 ft |

Sloan also provides numerous examples for gas mixtures and their resulting temperatures and pressures at which hydrates form. Suitable operating pressure/temperature combinations are determined on a case by case basis for each gas composition. Methods for estimating these operating conditions are described in Sloan. For example, for a typical light gas, operating at a pressure of about 300 psig and a temperature of about 10° C. should prevent hydrate formation.

To avoid hydrate formation, pressures less than the maximum pressure should be used. However, hydrate formation can also be controlled by kinetics and heat transfer. Thus, pressures near and/or above maximum can be used as long as the residence time is short.

Henry's Law constants for $CO_2$ and methane in pure water and sea water are:

|  | Methane | | Carbon Dioxide | |
|---|---|---|---|---|
| Temperature | 0° C. | 30° C. | 0° C. | 30° C. |
| Henry's Law Constant in Water (atm/mole fraction) | 22,000 | 42,000 | 740 | 1,850 |
| Henry's Law Constant in Sea Water (estimated) | 40,000 | | 740 | |

The above solubility data can be found, for example, in Clifford N. Click, "Applications of Henry's Law to Waste and Process Water VOC Emissions," 85$^{th}$ Annual Meeting Air and Waste Management Association. Click provides Henry's Law coefficients for several light hydrocarbon gases in water as a function of temperature and also provides an equation for the brine effect. In addition, Gianni Astartita, David Savage, and Attilio Bisio, "Gas Treating with Chemical Solvents," Wiley, pp. 208, contains a plot of the Henry's Law coefficient physical solubility of $CO_2$ into water as a function of temperature. Also, John Nighswander, Nicholas Kalogerakis, Anil Mehrotra, "Solubilities of Carbon Dioxide in Water and 1 wt % NaCl Solution at Pressures up to 10 Mpa and Temperatures From 80 to 200 Degrees C.," J. Chem. Eng. Data, 1989, 34, 355–360, discloses that the effect of salt on $CO_2$ solubility in water at temperatures of about 80 to about 200° C. and pressures of up to about 10 MPa is minimal.

The above data demonstrate that using sea water or operating at higher temperatures can enhance the selectivity of $CO_2$ removal. However, under some circumstances, use of sea water for scrubbing is impractical because of the introduction of sea water contaminants into the gas stream. This situation can occur, for example, when sea water is used to scrub $CO_2$ from a Fischer-Tropsch tail gas stream that is recycled to a Fischer-Tropsch or methane reformer reactor. Generally, such contamination should not hinder the use of sea water to scrub a fuel gas stream from a Fischer-Tropsch process derived from a tail gas.

Although the concept of isolating $CO_2$ from the atmosphere by injection into a marine environment, such as an ocean, or into terrestrial formations is not a novel concept, until now, no one has used aqueous streams, preferably at a pressure greater than about atmospheric pressure, to scrub $CO_2$ from a methane-containing gas and then disposed of the resulting $CO_2$-enriched aqueous stream by injection into at least one of a marine environment, a terrestrial formation, a combination thereof or the like. Instead, processes of the prior art merely disclose handling relatively pure $CO_2$ by processing gas through expensive gas compressors, liquefaction facilities or solidification facilities.

For example, U.S. Pat. No. 6,190,301, to Murray discloses a process and vehicle for disposal of $CO_2$. In Murray gaseous $CO_2$ is first solidified and then allowed to free fall in a marine environment through open water where it at least partially embeds itself in sedimentary formations. Sedimentation ensures that the marine environment serves as a carbon sink through carbonate sequestration. Thus, Murray describes converting gaseous $CO_2$ into a solid, requiring the use of expensive refrigeration and compression processes. Murray does not disclose dissolution of $CO_2$ using an aqueous phase, preferably at an elevated pressure, and disposal of a resulting $CO_2$-enriched aqueous stream in at least one of a marine environment, a terrestrial formation or combination thereof.

Similarly, U.S. Pat. No. 6,170,264 to Viteri discloses a low or no pollution engine for delivering power for vehicles or other power applications. Fuel and oxygen are combusted in a gas generator forming water and $CO_2$ with carbon-containing fuels. Combustion products, steam, carbon-containing fuels and $CO_2$ are passed through a condenser wherein the steam is condensed and the $CO_2$ is collected or discharged. The $CO_2$ is then compressed and cooled so that it is in a liquid or super critical state. The dense phase $CO_2$ is then further pressurized to a pressure matching a pressure, less hydrostatic head, existing deep within a porous geological formation, a deep aquifer, a deep ocean location or other terrestrial formation from which the return of $CO_2$ to the atmosphere is inhibited. Accordingly, Viteri discloses disposing of $CO_2$ from a power generation plant into the ocean or a terrestrial formation by first compressing and cooling $CO_2$ gas to form a liquid phase and then further compressing the liquid to match the hydrostatic head. Viteri does not describe isolating $CO_2$ from a methane-containing gas and then disposing of a resulting $CO_2$-enriched aqueous stream in at least one of a marine environment, a terrestrial formation or combination thereof.

United Kingdom Patent Application GB 2123027 to Mituyuki and Shinkichi describes the use of aqueous adsorbents to scrub $CO_2$ from synthesis gas streams (including those from a Fischer Tropsch unit) for the purpose of increasing the carbon oxide content of the syngas streams. This patent does not anticipate the use of scrubbing systems to remove carbon dioxide from the natural gas feedstock to a GTL facility and isolating it from the environment.

In contrast, the process of the present invention removes $CO_2$ from a methane-containing gas using an aqueous stream and disposes of the resulting $CO_2$-enriched aqueous stream without employing costly compression, liquefaction or solidification processes. Moreover, in the present invention, even if compression of the aqueous stream is desired, compression can be accomplished using relatively inexpensive liquid phase pumps.

Figure 2:
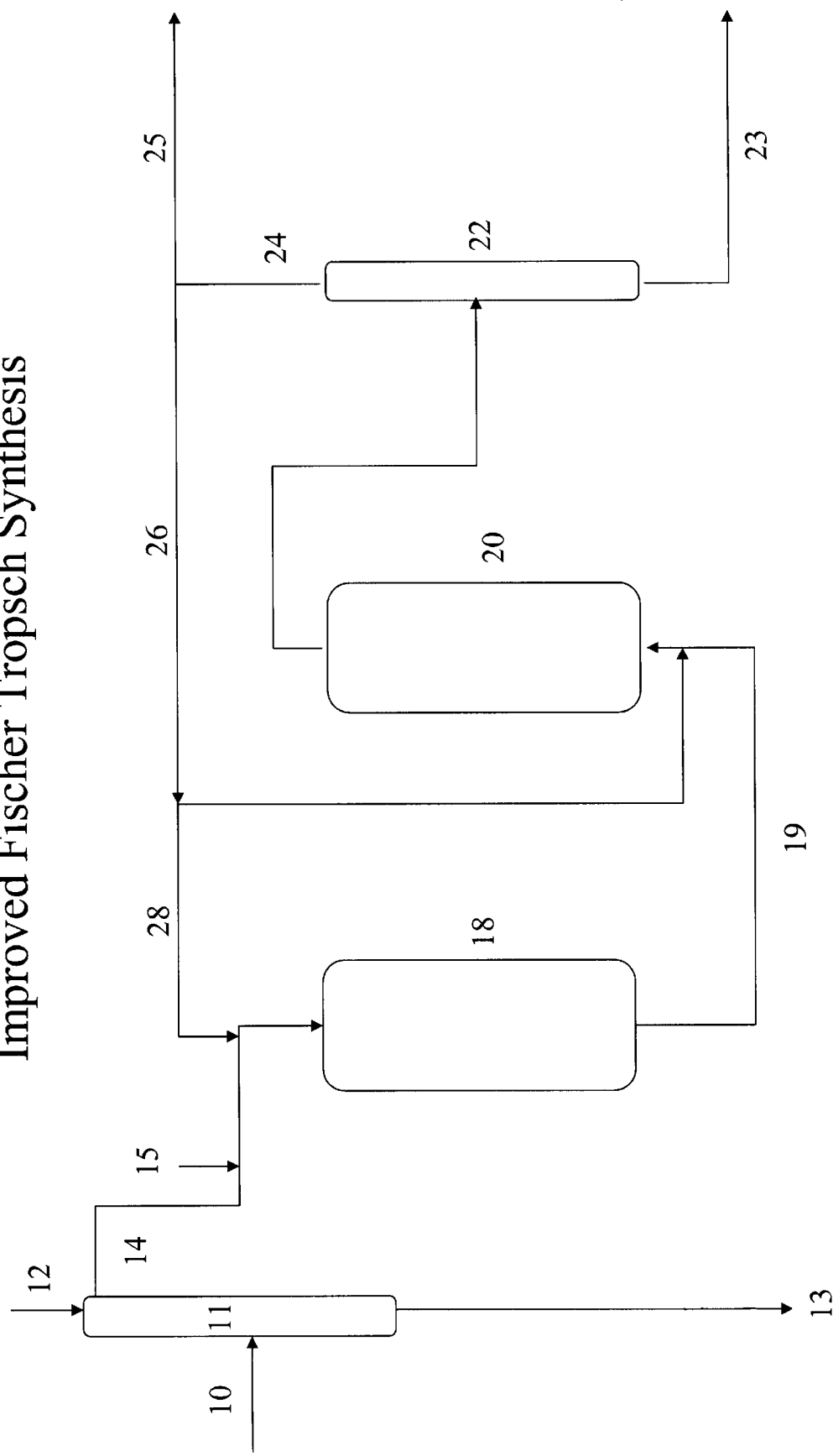
FIG. 2 is a schematic view of a preferred embodiment of a Fischer-Tropsch process according to the present invention.

A preferred embodiment of the present invention is depicted in FIG. 2. In this embodiment, a feed stream 10, comprising $CH_4$ and $CO_2$, enters a scrubber 11. A water stream 12 enters the scrubber 11 and a $CO_2$-enriched aqueous stream 13, exits the scrubber 11. A $CH_4$-containing stream containing a reduced $CO_2$ content 14 exits the scrubber 11. An $O_2$-and $H_2O$-containing stream 15 mixes with the $CH_4$-containing stream 14, creating a combined stream 16 that enters a synthesis gas formation reactor 18. A synthesis gas stream 19 exits the synthesis gas formation reactor 18 and enters a Fischer-Tropsch reactor 20. A Fischer-Tropsch process is conducted and a Fischer-Tropsch product stream 21 exits the Fischer-Tropsch reactor 20. The Fischer-Tropsch product stream 21 enters a separator 22. The separator 22 separates the Fischer-Tropsch product stream 21 into a hydrocarbon product stream 23, including $C_5^+$ liquids, and an unreacted gas stream 24, comprising unreacted CO, $H_2$ and $CO_2$. The unreacted gas stream 24 can be separated into an excess unreacted gas stream 25, comprising excess unreacted CO, $H_2$ and $CO_2$. The excess unreacted gas stream 25 is directed to a flare (not shown) where excess unreacted gases are disposed of by incineration. In addition, a portion of the unreacted gas stream 24 can be recirculated in a recirculation stream 26. A portion of the recirculated unreacted gas stream 26 can be recirculated in a recirculation stream 27 that mixes with the synthesis gas stream 19 before entering the Fischer-Tropsch reactor 20. Also, a portion of the recirculated unreacted gas stream 26 can be recirculated in a recirculation stream 28 to mix with the feed stream 16, creating a mixed stream 17 that enters the synthesis gas formation reactor 18. Finally, although not shown, the $CO_2$-containing aqueous stream 13 is disposed of by being injected into at least one of a marine environment, a terrestrial formation, combinations thereof or the like.

EXAMPLES

Example 1

$CO_2$ is removed from a natural gas source by scrubbing with sea water. A $CO_2$-rich source of natural gas is obtained from an undersea source, wherein the natural gas has the following approximate molar composition:

| | |
|---|---|
| $CH_4$ | 80% |
| $CO_2$ | 20% |
| $H_2S$ | trace. |

The gas is scrubbed in counter-current contact with de-aerated sea water at about 0° C. or about 30° C. and about 300 psig to remove approximately 90% of the $CO_2$ and to produce a gas having only about 2% $CO_2$. A pressure of about 300 psig is equivalent to a water depth of about 700 feet. The minimum amount of water needed per mole of gas, along with gas composition and selectivity, is as follows:

| | Temperature | |
|---|---|---|
| | 0° C. | 30° C. |
| Water required, gal/SCF gas (equilibrium limit) | 0.16 | 0.4 |
| Water required, gal/SCF gas (practical) | 0.19 | 0.5 |
| Scrubbing Gas Composition | | |
| Carbon Dioxide | 2 | 2 |
| Methane | 98 | 98 |
| Hydrogen Sulfide | low | low |
| Percent Removal | | |
| Carbon Dioxide | 90 | 90 |
| Methane loss | 3.2% | 4.4% |
| Hydrogen Sulfide | high | high |

As demonstrated in the above table, there are two water requirements: at equilibrium requirements and practical requirements. The equilibrium value is calculated with equilibrium constants. In practice, some additional water about 20%, is required to overcome slow transfer that may occur as adsorption approaches equilibrium, and to compensate for any slight effects due to dissolved air if non-de-aerated sea water is used as a scrubbing solution.

The above results show that scrubbing with sea water effectively removes $CO_2$ without causing an unacceptable loss in methane. In addition, the above-described process also provides the added benefit of removing hydrogen sulfide. Because hydrocarbon loss is minimized and water-flow requirements are reduced at lower temperatures, it is preferable to conduct processes of the present invention at relatively low temperatures.

While the present invention has been described with reference to specific embodiments, this application is intended to cover those various changes and substitutions that may be made by those of ordinary skill in the art without departing from the spirit and scope of the appended claims.

What is claimed is:

1. A method for removing $CO_2$ from a gas stream, the method comprising:

a. contacting a gas stream, comprising methane and $CO_2$, with an aqueous stream so that at least a portion of the $CO_2$ in the gas stream is dissolved into the aqueous stream, creating a $CO_2$-depleted gas stream having an enriched methane concentration and a $CO_2$-enriched aqueous stream, wherein the aqueous stream is at a pressure greater than about atmospheric pressure and less than a pressure of a source of the gas stream and wherein the aqueous stream has a pH of at least about 7.0;

b. separating the $CO_2$-enriched aqueous stream from the gas stream; and c. disposing of the $CO_2$-enriched aqueous stream in at least one of a marine environment, a terrestrial formation or combination thereof, wherein disposal of the $CO_2$-enriched aqueous stream is done at conditions sufficient to ensure that at least about 75% of the $CO_2$ removed from the gas stream remains dissolved in the aqueous stream.

2. The method of claim 1, wherein the aqueous stream is obtained from at least one of sea water, reaction water formed in a Fischer-Tropsch GTL process, spent cooling water from a Fischer-Tropsch GTL process, river water, non-potable water, water recovered from hydrocarbon production and combinations thereof.

3. The method of claim 1, wherein the terrestrial formation is selected from the group consisting essentially of a hydrocarbonaceous formation, a non-hydrocarbonaceous formation and combinations thereof.

4. A process for converting methane-containing gas in a Fischer-Tropsch GTL facility into liquid hydrocarbons, the process comprising:

a) contacting a methane-containing gas being supplied to a Fischer-Tropsch GTL facility, with an aqueous stream so that at least a portion of $CO_2$ in the methane-containing gas is dissolved into the aqueous stream creating a $CO_2$-depleted methane-containing gas and a $CO_2$-enriched aqueous stream, wherein upon contact with the methane-containing gas, the aqueous stream is at a pressure greater than about atmospheric pressure and less than a pressure of a source supplying the methane-containing gas and wherein before contact with the methane-containing gas, the aqueous stream has a pH of at least about 7.0;

b) separating the $CO_2$-enriched aqueous stream from the gas stream;

c) disposing of the $CO_2$-enriched aqueous stream in at least one of a marine environment, a terrestrial formation or combinations thereof wherein disposal of the $CO_2$-enriched aqueous stream is done at conditions sufficient to ensure that at least about 75% of the $CO_2$ removed from the gas stream remains dissolved in the aqueous stream; and d) processing the $CO_2$-depleted methane-containing gas in the Fischer-Tropsch GTL facility to obtain liquid hydrocarbons.

5. The process of claim 4, wherein the aqueous stream is selected from the group consisting essentially of sea water, reaction water formed in a Fischer-Tropsch GTL process, spent cooling water from a Fischer-Tropsch GTL process, river water, non-potable water, water recovered from hydrocarbon production and combinations thereof.

6. The process of claim 4, wherein the terrestrial formation is selected from the group consisting essentially of a hydrocarbonaceous formation, a non-hydrocarbonaceous formation and combinations thereof.

7. A method for removing $CO_2$ from a gas the method comprising:
  a) contacting a gas, comprising methane and $CO_2$, with a $CO_2$-selective adsorbent, at a pressure greater than about atmospheric pressure and less than a pressure of a source supplying the gas stream creating a $CO_2$-enriched adsorbent and a $CO_2$-depleted gas having an enriched methane concentration;
  b) treating the $CO_2$-enriched adsorbent, regenerating the adsorbent for recycling for reuse in step (a) and forming a $CO_2$ stream;
  c) contacting the $CO_2$ stream with an aqueous stream, so that at least a portion of the $CO_2$ is dissolved into the aqueous stream providing a $CO_2$-enriched aqueous stream, wherein the aqueous stream is at a pressure greater than about atmospheric pressure and less than a pressure of a source of the $CO_2$ stream and wherein prior to contact with the $CO_2$ stream, the aqueous stream has a pH of at least about 7.0; and
  d) disposing of the $CO_2$-enriched aqueous stream in at least one of a marine environment, a terrestrial formation or combination thereof wherein the disposal of the $CO_2$-enriched aqueous stream is done at a pressure sufficient to ensure that at least about 75% of the $CO_2$ removed from the $CO_2$ stream remains dissolved in the aqueous stream.

8. The method of claim 7, wherein the aqueous stream is obtained from at least one of sea water, reaction water formed in a Fischer-Tropsch GTL process, spent cooling water from a Fischer-Tropsch GTL process, river water, water, water recovered from hydrocarbon production and combinations thereof.

9. The process of claim 7, wherein the pressure is sufficient to ensure that at least about 90% of the $CO_2$ removed from the $CO_2$ stream remains dissolved in the aqueous stream.

10. The process of claim 7, wherein the terrestrial formation is selected from the group consisting essentially of a hydrocarbonaceous formation, a non-hydrocarbonaceous formation and combinations thereof.

11. A method for removing $CO_2$ from a gas stream, the method comprising:
  a) contacting a gas stream comprising methane and $CO_2$ with an aqueous stream selected from the group consisting of reaction water formed in a Fischer Tropsch GTL process, spent cooling water from a Fischer Tropsch GTL process, water recovered from hydrocarbon production, and mixtures thereof, at a pressure greater than about atmospheric pressure and less than a pressure of a source of the gas stream, so that at least a portion of the $CO_2$ in the gas stream is dissolved into the aqueous stream creating a $CO_2$-depleted gas stream, having an enriched methane concentration and a $CO_2$-enriched aqueous stream;
  b) separating the $CO_2$-enriched aqueous stream from the gas stream; and
  c) disposing of the $CO_2$-enriched aqueous stream in at least one of a marine environment, a terrestrial formation or combination thereof at a temperature, pressure and pH such that at least about 75% of the $CO_2$ removed from the gas stream remains dissolved in the aqueous stream.

12. An integrated process for converting methane-containing gas in a Fischer-Tropsch GTL facility into liquid hydrocarbons, the process comprising:
  a) contacting a methane-containing gas, being supplied to a Fischer-Tropsch GTL facility, with an aqueous stream comprising reaction water formed in the Fischer Tropsch GTL process, spent cooling water from the Fischer Tropsch GTL process, and mixtures thereof, at a pressure greater than about atmospheric pressure and less than a pressure of a source of the methane-containing gas, so that at least a portion of $CO_2$ in the methane-containing gas is dissolved into the aqueous stream, creating a $CO_2$-depleted methane-containing gas and a $CO_2$-enriched aqueous stream;
  b) separating the $CO_2$-enriched aqueous stream from the gas stream;
  c) disposing of the $CO_2$-enriched aqueous stream in at least one of a marine environment, a terrestrial formation or combination thereof at a temperature, pressure and pH such that at least about 75% of the $CO_2$ removed from the gas stream remains dissolved in the aqueous stream;
  d) processing the $CO_2$-depleted methane-containing gas in the Fischer-Tropsch GTL facility to obtain liquid hydrocarbons;
  e) isolating a least a portion of the reaction water formed in the Fischer Tropsch process, the spent cooling water from the Fischer Tropsch process, or mixtures thereof to provide an aqueous stream; and
  f) recycling the aqueous stream to contact the methane-containing gas.

13. The process of claim 12, wherein prior to contact with the methane containing gas, the aqueous stream has a pH of greater than 7.0.

14. The process of claim 13, wherein the pH of the aqueous stream is increased by adding an alkali material, adding ammonia, adding a base, or combinations thereof.

15. The process of claim 1, further comprising adjusting the pH of the aqueous stream with a basic material prior to contacting the aqueous stream with the gas stream.

16. The process of claim 15, further comprising, de-aerating the aqueous stream prior to contacting the aqueous stream with the gas stream.

17. The process of claim 12, further comprising adjusting the pH of the aqueous stream with a basic material prior to contacting the aqueous stream with the gas stream.

18. The process of claim 17, further comprising, de-aerating the aqueous stream prior to contacting the aqueous stream with the gas stream.

* * * * *

UNITED STATES PATENT AND TRADEMARK OFFICE
CERTIFICATE OF CORRECTION

PATENT NO. : 6,667,347 B2
DATED : December 23, 2003
INVENTOR(S) : Dennis J. O'Rear et al.

It is certified that error appears in the above-identified patent and that said Letters Patent is hereby corrected as shown below:

<u>Column 14,</u>
Line 32, "e) isolating a least a portion of the reaction water formed" should read
-- e) isolating at least a portion of the reaction water formed --.

Signed and Sealed this

Twenty-fourth Day of February, 2004

JON W. DUDAS
*Acting Director of the United States Patent and Trademark Office*